(12) United States Patent
Neculescu et al.

(10) Patent No.: US 7,316,840 B2
(45) Date of Patent: Jan. 8, 2008

(54) STRAND-REINFORCED COMPOSITE MATERIAL

(75) Inventors: Cristian M. Neculescu, Neenah, WI (US); Peiguang Zhou, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 375 days.

(21) Appl. No.: 10/187,761

(22) Filed: Jul. 2, 2002

(65) Prior Publication Data

US 2004/0005832 A1    Jan. 8, 2004

(51) Int. Cl.
*B32B 27/04* (2006.01)
*B32B 27/00* (2006.01)
*A41B 9/00* (2006.01)

(52) U.S. Cl. .............. 428/297.4; 428/298.1; 428/299.7; 2/400; 442/328; 442/329

(58) Field of Classification Search .......... 428/152, 428/182, 283, 284, 297, 298, 299, 326, 903, 428/913, 297.4, 298.1, 299.7; 2/400, 403; 604/358; 442/328, 329
See application file for complete search history.

(56) References Cited

U.S. PATENT DOCUMENTS

| | | | |
|---|---|---|---|
| 2,206,761 A | 7/1940 | Bergstein |
| 2,266,761 A | 12/1941 | Jackson, Jr. et al. |
| 2,357,392 A | 9/1944 | Francis, Jr. |
| 2,464,301 A | 3/1949 | Francis, Jr. |
| 2,483,405 A | 10/1949 | Francis, Jr. |
| 2,957,512 A | 10/1960 | Wade et al. |
| 2,957,852 A | 10/1960 | Frankenburg et al. |
| 3,186,893 A | 6/1965 | Mercer |
| 3,338,992 A | 8/1967 | Kinney |
| 3,341,394 A | 9/1967 | Kinney |
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |
| 3,468,748 A | 9/1969 | Bassett |
| 3,489,148 A | 1/1970 | Duncan et al. |
| 3,502,538 A | 3/1970 | Petersen |
| 3,502,763 A | 3/1970 | Hartmann |
| 3,542,615 A | 11/1970 | Dobo et al. |
| 3,575,782 A | 4/1971 | Hansen |
| 3,616,129 A | 10/1971 | Sager |
| 3,629,047 A | 12/1971 | Davison |
| 3,669,823 A | 6/1972 | Wood |
| 3,673,026 A | 6/1972 | Brown |
| 3,676,242 A | 7/1972 | Prentice |
| 3,689,342 A | 9/1972 | Vogt et al. |

(Continued)

FOREIGN PATENT DOCUMENTS

CA     2165486    6/1996

(Continued)

*Primary Examiner*—N. Edwards
(74) *Attorney, Agent, or Firm*—Pauley Petersen Erickson

(57) ABSTRACT

Elastomeric composites and elastomeric composite laminates including reinforcement strands incorporated into an elastomeric adhesive film. The strands may vary in terms of levels of tension. Facing layers, such as nonwoven webs, can be laminated to both surfaces of the elastomeric composite to form laminates. A method of making such composites and laminates involves adjusting tension among various elastic strands while extruding the elastic strands and incorporating the elastic strands into the elastomeric adhesive film.

34 Claims, 5 Drawing Sheets

U.S. PATENT DOCUMENTS

| | | |
|---|---|---|
| 3,692,618 A | 9/1972 | Dorschner et al. |
| 3,752,613 A | 8/1973 | Vogt et al. |
| 3,773,590 A | 11/1973 | Morgan |
| 3,802,817 A | 4/1974 | Matsuki et al. |
| 3,806,289 A | 4/1974 | Schwarz |
| 3,836,416 A | 9/1974 | Ropiequet |
| 3,838,692 A | 10/1974 | Levesque |
| 3,849,241 A | 11/1974 | Butin et al. |
| 3,857,144 A | 12/1974 | Bustin |
| 3,860,003 A | 1/1975 | Buell |
| 3,890,184 A | 6/1975 | Morgan |
| 3,904,465 A | 9/1975 | Haase et al. |
| 3,912,567 A | 10/1975 | Schwartz |
| 3,917,448 A | 11/1975 | Wood |
| 3,932,328 A | 1/1976 | Korpman |
| 3,949,128 A | 4/1976 | Ostermeier |
| 3,949,130 A | 4/1976 | Sabee et al. |
| 3,973,063 A | 8/1976 | Clayton |
| 3,978,185 A | 8/1976 | Buntin et al. |
| 3,979,050 A | 9/1976 | Cilia |
| 4,013,816 A | 3/1977 | Sabee et al. |
| 4,028,292 A | 6/1977 | Korpman |
| 4,038,346 A | 7/1977 | Feeney |
| 4,080,348 A | 3/1978 | Korpman |
| 4,090,385 A | 5/1978 | Packard |
| 4,107,364 A | 8/1978 | Sisson |
| 4,135,037 A | 1/1979 | Udipi et al. |
| 4,148,676 A | 4/1979 | Paquette et al. |
| 4,209,563 A | 6/1980 | Sisson |
| 4,211,807 A | 7/1980 | Yazawa et al. |
| 4,239,578 A | 12/1980 | Gore |
| 4,241,123 A | 12/1980 | Shih |
| 4,248,652 A | 2/1981 | Civardi et al. |
| 4,259,220 A | 3/1981 | Bunnelle et al. |
| 4,285,998 A | 8/1981 | Thibodeau |
| 4,300,562 A | 11/1981 | Pieniak |
| 4,302,495 A | 11/1981 | Marra |
| 4,303,571 A | 12/1981 | Jansen et al. |
| 4,304,234 A | 12/1981 | Hartmann |
| 4,310,594 A | 1/1982 | Yamazaki et al. |
| 4,319,572 A | 3/1982 | Widlund et al. |
| 4,323,534 A | 4/1982 | DesMarais |
| 4,333,782 A | 6/1982 | Pieniak |
| 4,340,558 A | 7/1982 | Hendrickson |
| 4,340,563 A | 7/1982 | Appel et al. |
| 4,375,446 A | 3/1983 | Fujii et al. |
| 4,402,688 A | 9/1983 | Julemont |
| 4,405,397 A | 9/1983 | Teed |
| 4,413,623 A | 11/1983 | Pieniak |
| 4,417,935 A | 11/1983 | Spencer |
| 4,418,123 A | 11/1983 | Bunnelle et al. |
| 4,438,167 A | 3/1984 | Schwarz |
| 4,440,819 A | 4/1984 | Rosser et al. |
| 4,490,427 A | 12/1984 | Grant et al. |
| 4,496,417 A | 1/1985 | Haake et al. |
| 4,500,316 A | 2/1985 | Damico |
| 4,507,163 A | 3/1985 | Menard |
| 4,522,863 A | 6/1985 | Keck et al. |
| 4,525,407 A | 6/1985 | Ness |
| 4,543,099 A | 9/1985 | Bunnelle et al. |
| 4,548,859 A | 10/1985 | Kline et al. |
| 4,552,795 A | 11/1985 | Hansen et al. |
| 4,555,811 A | 12/1985 | Shimalla |
| 4,572,752 A | 2/1986 | Jensen et al. |
| 4,586,199 A | 5/1986 | Birring |
| D284,036 S | 6/1986 | Birring |
| 4,592,938 A * | 6/1986 | Benoit ................. 428/35.5 |
| 4,606,964 A | 8/1986 | Wideman |
| 4,618,384 A | 10/1986 | Sabee |
| 4,626,305 A | 12/1986 | Suzuki et al. |
| 4,636,419 A | 1/1987 | Madsen et al. |
| 4,640,859 A | 2/1987 | Hansen et al. |
| 4,644,045 A | 2/1987 | Fowells |
| 4,652,487 A | 3/1987 | Morman |
| 4,656,081 A | 4/1987 | Ando et al. |
| 4,657,793 A | 4/1987 | Fisher |
| 4,657,802 A | 4/1987 | Morman |
| 4,661,389 A | 4/1987 | Mudge et al. |
| 4,663,220 A | 5/1987 | Wisneski et al. |
| 4,666,543 A | 5/1987 | Kawano |
| 4,675,068 A | 6/1987 | Lundmark |
| 4,683,877 A | 8/1987 | Ersfeld et al. |
| 4,687,477 A | 8/1987 | Suzuki et al. |
| 4,692,368 A | 9/1987 | Taylor et al. |
| 4,692,371 A | 9/1987 | Morman et al. |
| 4,698,242 A | 10/1987 | Salerno |
| 4,704,116 A | 11/1987 | Enloe |
| 4,718,901 A | 1/1988 | Singheimer |
| 4,719,261 A | 1/1988 | Bunnelle et al. |
| 4,720,415 A | 1/1988 | Vander Wielen et al. |
| 4,725,468 A | 2/1988 | McIntyre |
| 4,726,874 A | 2/1988 | VanVliet |
| 4,734,311 A | 3/1988 | Sokolowski |
| 4,734,320 A | 3/1988 | Ohira et al. |
| 4,734,447 A | 3/1988 | Hattori et al. |
| 4,735,673 A | 4/1988 | Piron |
| 4,756,942 A | 7/1988 | Aichele |
| 4,761,198 A | 8/1988 | Salerno |
| 4,762,582 A | 8/1988 | de Jonckheere |
| 4,775,579 A | 10/1988 | Hagy et al. |
| 4,777,080 A | 10/1988 | Harris, Jr. et al. |
| 4,789,699 A | 12/1988 | Kieffer et al. |
| 4,798,603 A | 1/1989 | Meyer et al. |
| 4,801,345 A | 1/1989 | Dussaud et al. |
| 4,801,482 A | 1/1989 | Goggans et al. |
| 4,803,117 A | 2/1989 | Daponte |
| 4,804,577 A | 2/1989 | Hazelton et al. |
| 4,818,597 A | 4/1989 | DaPonte et al. |
| 4,826,415 A | 5/1989 | Mende |
| 4,837,715 A | 6/1989 | Ungpiyakul et al. |
| 4,842,666 A | 6/1989 | Werenicz |
| 4,854,985 A | 8/1989 | Soderlund et al. |
| 4,854,989 A | 8/1989 | Singheimer |
| 4,863,779 A | 9/1989 | Daponte |
| 4,867,735 A | 9/1989 | Wogelius |
| 4,874,447 A | 10/1989 | Hazelton et al. |
| 4,879,170 A * | 11/1989 | Radwanski et al. ......... 442/329 |
| 4,883,482 A | 11/1989 | Gandrez et al. |
| 4,883,549 A | 11/1989 | Frost et al. |
| 4,891,258 A | 1/1990 | Fahrenkrug |
| 4,892,536 A | 1/1990 | DesMarais et al. |
| 4,892,903 A | 1/1990 | Himes |
| 4,900,619 A | 2/1990 | Ostrowski et al. |
| 4,906,507 A | 3/1990 | Grynaeus et al. |
| 4,908,247 A | 3/1990 | Baird et al. |
| 4,908,253 A | 3/1990 | Rasmussen |
| 4,910,064 A | 3/1990 | Sabee |
| 4,917,696 A | 4/1990 | De Jonckheere |
| 4,917,746 A | 4/1990 | Kons et al. |
| 4,929,492 A | 5/1990 | Carey, Jr. et al. |
| 4,935,021 A | 6/1990 | Huffman et al. |
| 4,938,757 A | 7/1990 | Van Gompel et al. |
| 4,938,821 A | 7/1990 | Soderlund et al. |
| 4,939,016 A * | 7/1990 | Radwanski et al. ......... 428/152 |
| 4,940,464 A | 7/1990 | Van Gompel et al. |
| 4,965,122 A | 10/1990 | Morman |
| 4,968,313 A | 11/1990 | Sabee |
| 4,970,259 A | 11/1990 | Mitchell et al. |
| 4,977,011 A | 12/1990 | Smith |
| 4,984,584 A | 1/1991 | Hansen et al. |
| 4,994,508 A | 2/1991 | Shiraki et al. |
| 4,995,928 A | 2/1991 | Sabee |
| 4,998,929 A | 3/1991 | Bjorksund et al. |
| 5,000,806 A | 3/1991 | Merkatoris et al. |

| | | | | | | |
|---|---|---|---|---|---|---|
| 5,002,815 A | 3/1991 | Yamanaka et al. | | 5,405,682 A | 4/1995 | Shawyer et al. |
| 5,005,215 A | 4/1991 | McIlquham | | 5,407,507 A | 4/1995 | Ball |
| 5,013,785 A | 5/1991 | Mizui | | 5,411,618 A | 5/1995 | Jocewicz, Jr. |
| 5,028,646 A | 7/1991 | Miller et al. | | 5,413,654 A | 5/1995 | Igaue et al. |
| 5,032,120 A | 7/1991 | Freeland et al. | | 5,413,849 A | 5/1995 | Austin et al. |
| 5,034,008 A | 7/1991 | Breitkopf | | 5,415,644 A | 5/1995 | Enloe |
| 5,045,133 A | 9/1991 | DaPonte et al. | | 5,415,649 A | 5/1995 | Watanabe et al. |
| 5,046,272 A | 9/1991 | Vogt et al. | | 5,415,925 A | 5/1995 | Austin et al. |
| 5,060,349 A | 10/1991 | Walton et al. | | 5,422,172 A | 6/1995 | Wu |
| 5,073,436 A | 12/1991 | Antonacci et al. | | 5,425,987 A | 6/1995 | Shawver et al. |
| 5,093,422 A | 3/1992 | Himes | | 5,429,629 A | 7/1995 | Latimer et al. |
| 5,100,435 A | 3/1992 | Onwumere | | 5,429,694 A | 7/1995 | Herrmann |
| 5,104,116 A | 4/1992 | Pohjola | | 5,429,856 A * | 7/1995 | Krueger et al. ............. 604/370 |
| 5,108,820 A | 4/1992 | Kaneko et al. | | 5,431,644 A | 7/1995 | Sipinen et al. |
| 5,112,889 A | 5/1992 | Miller et al. | | 5,431,991 A | 7/1995 | Quantrille et al. |
| 5,114,087 A | 5/1992 | Fisher et al. | | 5,447,462 A | 9/1995 | Smith et al. |
| 5,116,662 A | 5/1992 | Morman | | 5,447,508 A | 9/1995 | Numano et al. |
| 5,147,487 A | 9/1992 | Nomura et al. | | 5,449,353 A | 9/1995 | Watanabe et al. |
| 5,149,741 A | 9/1992 | Alper et al. | | 5,464,401 A | 11/1995 | Hasse et al. |
| 5,163,932 A | 11/1992 | Nomura et al. | | 5,472,775 A | 12/1995 | Obijeski et al. |
| D331,627 S | 12/1992 | Igaue et al. | | 5,476,458 A | 12/1995 | Glaug et al. |
| 5,169,706 A | 12/1992 | Collier, IV et al. | | 5,476,563 A | 12/1995 | Nakata |
| 5,169,712 A | 12/1992 | Tapp | | 5,484,645 A | 1/1996 | Lickfield et al. |
| 5,176,668 A | 1/1993 | Bernardin | | 5,486,166 A | 1/1996 | Bishop et al. |
| 5,176,672 A | 1/1993 | Bruemmer et al. | | 5,490,846 A | 2/1996 | Ellis et al. |
| 5,181,562 A * | 1/1993 | Kuriki ........................ 165/166 | | 5,496,298 A | 3/1996 | Kuepper et al. |
| 5,186,779 A | 2/1993 | Tubbs | | 5,498,468 A | 3/1996 | Blaney |
| 5,192,606 A | 3/1993 | Proxmire et al. | | 5,500,075 A | 3/1996 | Herrmann |
| 5,198,281 A | 3/1993 | Muzzy et al. | | 5,501,679 A | 3/1996 | Krueger et al. |
| 5,200,246 A | 4/1993 | Sabee | | 5,509,915 A | 4/1996 | Hanson et al. |
| 5,204,429 A | 4/1993 | Kaminsky et al. | | 5,514,470 A | 5/1996 | Haffner et al. |
| D335,707 S | 5/1993 | Igaue et al. | | 5,516,476 A | 5/1996 | Haggard et al. |
| 5,209,801 A | 5/1993 | Smith | | 5,523,146 A | 6/1996 | Bodford et al. |
| 5,219,633 A | 6/1993 | Sabee | | 5,527,300 A | 6/1996 | Sauer |
| 5,224,405 A | 7/1993 | Pohjola | | 5,531,850 A | 7/1996 | Herrmann |
| 5,226,992 A | 7/1993 | Morman | | 5,534,330 A | 7/1996 | Groshens |
| 5,229,191 A | 7/1993 | Austin | | 5,536,563 A | 7/1996 | Shah et al. |
| 5,232,777 A | 8/1993 | Sipinen et al. | | 5,540,796 A | 7/1996 | Fries |
| 5,236,430 A | 8/1993 | Bridges | | 5,540,976 A | 7/1996 | Shawver et al. |
| 5,236,770 A | 8/1993 | Assent et al. | | 5,543,206 A | 8/1996 | Austin et al. |
| 5,238,733 A | 8/1993 | Joseph et al. | | 5,545,158 A | 8/1996 | Jessup |
| 5,246,433 A | 9/1993 | Hasse et al. | | 5,545,285 A | 8/1996 | Johnson |
| D340,283 S | 10/1993 | Igaue et al. | | 5,549,964 A | 8/1996 | Shohji et al. |
| 5,252,170 A | 10/1993 | Schaupp | | 5,569,232 A | 10/1996 | Roe et al. |
| 5,259,902 A | 11/1993 | Muckenfuhs | | 5,575,783 A | 11/1996 | Clear et al. |
| 5,260,126 A | 11/1993 | Collier, IV et al. | | 5,576,090 A | 11/1996 | Suzuki |
| 5,272,236 A | 12/1993 | Lai et al. | | 5,582,668 A | 12/1996 | Kling |
| 5,278,272 A | 1/1994 | Lai et al. | | 5,591,152 A | 1/1997 | Buell et al. |
| 5,288,791 A | 2/1994 | Collier, IV et al. | | 5,591,792 A | 1/1997 | Hattori et al. |
| 5,290,842 A | 3/1994 | Sasaki et al. | | 5,595,618 A | 1/1997 | Fries et al. |
| 5,296,080 A | 3/1994 | Merkatoris et al. | | 5,597,430 A | 1/1997 | Rasche |
| 5,304,599 A | 4/1994 | Himes | | 5,612,118 A | 3/1997 | Schleinz et al. |
| 5,308,345 A | 5/1994 | Herrin | | 5,614,276 A | 3/1997 | Petsetakis |
| 5,312,500 A | 5/1994 | Kurihara et al. | | 5,620,780 A | 4/1997 | Krueger et al. |
| 5,324,580 A | 6/1994 | Allan et al. | | 5,624,740 A | 4/1997 | Nakata |
| 5,332,613 A | 7/1994 | Taylor et al. | | 5,626,573 A | 5/1997 | Igaue et al. |
| 5,334,437 A | 8/1994 | Zafiroglu | | 5,628,856 A | 5/1997 | Dobrin et al. |
| 5,334,446 A | 8/1994 | Quantrille et al. | | 5,645,672 A | 7/1997 | Dobrin |
| 5,336,545 A | 8/1994 | Morman | | 5,652,041 A | 7/1997 | Buerger et al. |
| 5,336,552 A | 8/1994 | Strack et al. | | 5,660,664 A | 8/1997 | Herrmann |
| 5,342,341 A | 8/1994 | Igaue et al. | | 5,663,228 A | 9/1997 | Sasaki et al. |
| 5,342,469 A | 8/1994 | Bodford et al. | | 5,669,897 A | 9/1997 | Lavon et al. |
| 5,360,854 A | 11/1994 | Bozich, Jr. | | 5,674,216 A | 10/1997 | Buell et al. |
| 5,364,382 A | 11/1994 | Latimer et al. | | 5,680,653 A | 10/1997 | Mathis et al. |
| 5,366,793 A | 11/1994 | Fitts, Jr. et al. | | 5,681,302 A | 10/1997 | Melbye et al. |
| 5,376,198 A | 12/1994 | Fahrenkrug et al. | | 5,683,787 A | 11/1997 | Boich et al. |
| 5,376,430 A | 12/1994 | Swenson et al. | | 5,690,626 A | 11/1997 | Suzuki et al. |
| 5,382,400 A | 1/1995 | Pike et al. | | 5,691,034 A | 11/1997 | Krueger et al. |
| 5,385,775 A | 1/1995 | Wright | | 5,693,038 A | 12/1997 | Suzuki et al. |
| 5,389,173 A | 2/1995 | Merkatoris et al. | | 5,695,849 A | 12/1997 | Shawver et al. |
| 5,389,438 A | 2/1995 | Miller et al. | | 5,702,378 A | 12/1997 | Widlund et al. |
| 5,393,599 A | 2/1995 | Quantrille et al. | | 5,707,709 A | 1/1998 | Blake |
| 5,399,219 A | 3/1995 | Roessler et al. | | 5,709,921 A | 1/1998 | Shawver |

| | | | | | | |
|---|---|---|---|---|---|---|
| 5,720,838 | A | 2/1998 | Nakata | 6,123,694 | A | 9/2000 | Pieniak et al. |
| 5,733,635 | A | 3/1998 | Terakawa et al. | 6,132,410 | A | 10/2000 | Van Gompel et al. |
| 5,733,822 | A | 3/1998 | Gessner et al. | 6,149,637 | A | 11/2000 | Allen et al. |
| 5,735,839 | A | 4/1998 | Kawaguchi et al. | 6,152,904 | A | 11/2000 | Matthews et al. |
| 5,736,219 | A | 4/1998 | Suehr et al. | 6,169,848 | B1 | 1/2001 | Henry |
| 5,746,731 | A | 5/1998 | Hisada | 6,183,587 | B1 | 2/2001 | McFall et al. |
| 5,749,865 | A | 5/1998 | Yamamoto et al. | 6,183,847 | B1 | 2/2001 | Goldwasser |
| 5,749,866 | A | 5/1998 | Roe et al. | 6,197,845 | B1 | 3/2001 | Janssen et al. |
| 5,766,389 | A | 6/1998 | Brandon et al. | 6,214,476 | B1 | 4/2001 | Ikeda et al. |
| 5,766,737 | A | 6/1998 | Willey et al. | 6,217,690 | B1 | 4/2001 | Rajala et al. |
| 5,769,838 | A | 6/1998 | Buell et al. | 6,231,557 | B1 | 5/2001 | Krautkramer et al. |
| 5,769,993 | A | 6/1998 | Baldauf | 6,238,379 | B1 | 5/2001 | Keuhn, Jr. et al. |
| 5,772,649 | A | 6/1998 | Siudzinski | 6,245,050 | B1 | 6/2001 | Odorzynski et al. |
| 5,773,373 | A | 6/1998 | Wynne et al. | 6,245,168 | B1 | 6/2001 | Coenen et al. |
| 5,773,374 | A | 6/1998 | Wood et al. | 6,260,211 | B1 | 7/2001 | Rajala et al. |
| 5,788,804 | A | 8/1998 | Horsting | 6,279,807 | B1 | 8/2001 | Crowley et al. |
| 5,789,065 | A | 8/1998 | Haffner et al. | 6,290,979 | B1 | 9/2001 | Roe et al. |
| 5,789,328 | A | 8/1998 | Kurihara et al. | 6,310,164 | B1 | 10/2001 | Morizono et al. |
| 5,789,474 | A | 8/1998 | Lu et al. | 6,316,013 | B1 | 11/2001 | Paul et al. |
| 5,790,983 | A | 8/1998 | Rosch et al. | 6,316,687 | B1 | 11/2001 | Davis et al. |
| 5,800,903 | A | 9/1998 | Wood et al. | 6,316,688 | B1 | 11/2001 | Hammons et al. |
| 5,804,021 | A | 9/1998 | Abuto et al. | 6,320,096 | B1 | 11/2001 | Inoue et al. |
| 5,804,286 | A | 9/1998 | Quantrille et al. | 6,323,389 | B1 | 11/2001 | Thomas et al. |
| 5,814,176 | A | 9/1998 | Proulx | 6,329,459 | B1 | 12/2001 | Kang et al. |
| 5,817,087 | A | 10/1998 | Takabayashi et al. | 6,364,863 | B1 | 4/2002 | Yamamoto et al. |
| 5,818,719 | A | 10/1998 | Brandon et al. | 6,365,659 | B1 | 4/2002 | Aoyama et al. |
| 5,830,203 | A | 11/1998 | Suzuki et al. | 6,367,089 | B2 | 4/2002 | Van Gompel et al. |
| 5,834,089 | A | 11/1998 | Jones et al. | 6,475,600 | B1 | 11/2002 | Morman et al. |
| 5,836,931 | A | 11/1998 | Toyoda et al. | 6,537,935 | B1 | 3/2003 | Seth et al. |
| 5,836,932 | A | 11/1998 | Buell et al. | 6,582,810 | B2 * | 6/2003 | Heffelfinger ............ 428/297.4 |
| 5,840,412 | A | 11/1998 | Wood et al. | 6,767,852 | B2 | 7/2004 | Friderich et al. |
| 5,840,633 | A | 11/1998 | Kurihara et al. | 6,967,178 | B2 * | 11/2005 | Zhou et al. ................. 442/149 |
| 5,846,232 | A | 12/1998 | Serbiak et al. | 6,978,486 | B2 * | 12/2005 | Zhou et al. .................... 2/400 |
| 5,849,001 | A | 12/1998 | Torimae et al. | 7,015,155 | B2 * | 3/2006 | Zhou et al. ................. 442/149 |
| 5,856,387 | A | 1/1999 | Sasaki et al. | 2002/0002021 | A1 | 1/2002 | May et al. |
| 5,860,945 | A | 1/1999 | Cramer et al. | 2002/0009940 | A1 | 1/2002 | May et al. |
| 5,865,933 | A | 2/1999 | Morin et al. | 2002/0019616 | A1 | 2/2002 | Thomas |
| 5,876,392 | A | 3/1999 | Hisada | 2002/0072561 | A1 | 6/2002 | Johoji et al. |
| 5,879,776 | A | 3/1999 | Nakata | 2002/0081423 | A1 | 6/2002 | Heffelfinger |
| 5,882,573 | A | 3/1999 | Kwok et al. | 2002/0104608 | A1 | 8/2002 | Welch et al. |
| 5,885,656 | A | 3/1999 | Goldwasser | 2002/0138063 | A1 | 9/2002 | Kuen et al. |
| 5,885,686 | A | 3/1999 | Cederblad et al. | 2002/0164465 | A1 | 11/2002 | Curro et al. |
| 5,897,546 | A | 4/1999 | Kido et al. | 2004/0005832 | A1 | 1/2004 | Neculescu et al. |
| 5,899,895 | A | 5/1999 | Robles et al. | 2004/0005834 | A1 | 1/2004 | Zhou et al. |
| 5,902,540 | A | 5/1999 | Kwok | 2004/0006324 | A1 | 1/2004 | Zhou et al. |
| 5,904,298 | A | 5/1999 | Kwok et al. | 2004/0127128 | A1 | 7/2004 | Thomas |
| 5,916,206 | A | 6/1999 | Otsubo et al. | | | | |
| 5,921,973 | A | 7/1999 | Newkirk et al. | | | | |

FOREIGN PATENT DOCUMENTS

| | | |
|---|---|---|
| DE | 34 23 644 | 1/1986 |
| DE | 37 34 963 | 4/1988 |
| EP | 0 155 636 | 9/1985 |
| EP | 0 172 037 | 2/1986 |
| EP | 0 217 032 | 4/1987 |
| EP | 0 239 080 | 9/1987 |
| EP | 0 330 716 A2 | 9/1989 |
| EP | 0 380 781 | 8/1990 |
| EP | 0 396 800 | 11/1990 |
| EP | 0 456 885 | 11/1991 |
| EP | 0 547 497 | 6/1993 |
| EP | 0 582 569 | 2/1994 |
| EP | 0 604 731 | 7/1994 |
| EP | 0 617 939 | 10/1994 |
| EP | 0 688 550 | 12/1995 |
| EP | 0 689 815 | 1/1996 |
| EP | 0 713 546 | 5/1996 |
| EP | 0 743 052 | 11/1996 |
| EP | 0 753 292 | 1/1997 |
| EP | 0 761 193 | 3/1997 |
| EP | 0 761 194 | 3/1997 |
| EP | 0 763 353 | 3/1997 |
| EP | 0 787 474 | 8/1997 |
| EP | 0 802 251 A1 | 10/1997 |

Additional rows in first table:

| | | | |
|---|---|---|---|
| 5,930,139 | A | 7/1999 | Chapdelaine et al. |
| 5,931,581 | A | 8/1999 | Garberg et al. |
| 5,932,039 | A | 8/1999 | Popp et al. |
| 5,938,648 | A | 8/1999 | LaVon et al. |
| 5,941,865 | A | 8/1999 | Otsubo et al. |
| D414,262 | S | 9/1999 | Ashton et al. |
| 5,952,252 | A | 9/1999 | Shawver et al. |
| 5,964,970 | A | 10/1999 | Woolwine et al. |
| 5,964,973 | A | 10/1999 | Heath et al. |
| 5,990,377 | A | 11/1999 | Chen et al. |
| 5,993,433 | A | 11/1999 | St. Louis et al. |
| 5,997,521 | A | 12/1999 | Robles et al. |
| 6,004,306 | A | 12/1999 | Robles et al. |
| 6,009,558 | A | 1/2000 | Rosch et al. |
| 6,033,502 | A | 3/2000 | Coenen et al. |
| 6,045,543 | A | 4/2000 | Pozniak et al. |
| 6,048,326 | A | 4/2000 | Davis et al. |
| 6,057,024 | A * | 5/2000 | Mleziva et al. ............. 428/114 |
| 6,066,369 | A | 5/2000 | Schulz et al. |
| 6,075,179 | A * | 6/2000 | McCormack et al. ....... 604/367 |
| 6,087,550 | A | 7/2000 | Anderson-Fischer et al. |
| 6,090,234 | A | 7/2000 | Barone et al. |
| 6,092,002 | A | 7/2000 | Kastman et al. |
| 6,093,663 | A | 7/2000 | Ouellette et al. |
| 6,096,668 | A | 8/2000 | Abuto et al. |

| | | |
|---|---|---|
| EP | 0 806 196 | 11/1997 |
| EP | 0 814 189 | 12/1997 |
| EP | 0 873 738 | 10/1998 |
| EP | 0 888 101 | 1/1999 |
| EP | 0 901 780 | 3/1999 |
| EP | 1 013 251 | 6/2000 |
| GB | 2 244 422 | 12/1991 |
| GB | 2 250 921 | 6/1992 |
| GB | 2 253 131 | 9/1992 |
| GB | 2 267 024 | 11/1993 |
| GB | 2 268 389 | 1/1994 |
| IS | 92891 | 2/1992 |
| JP | 3-67646 | 3/1991 |
| WO | WO 80/00676 | 4/1980 |
| WO | WO 90/03464 | 4/1990 |
| WO | WO 91/07277 | 5/1991 |
| WO | WO 92/16371 | 10/1992 |
| WO | WO 93/15247 | 8/1993 |
| WO | WO 93/17648 | 9/1993 |
| WO | WO 94/09736 | 5/1994 |
| WO | WO 95/03443 | 2/1995 |
| WO | WO 95/04182 | 2/1995 |
| WO | WO 95/16425 | 6/1995 |
| WO | WO 95/16562 | 6/1995 |
| WO | WO 95/34264 | 12/1995 |
| WO | WO 96/13989 | 5/1996 |
| WO | WO 96/23466 | 8/1996 |
| WO | WO 96/35402 | 11/1996 |
| WO | WO 97/17046 | 5/1997 |
| WO | WO 98/14156 | 4/1998 |
| WO | WO 98/49988 | 11/1998 |
| WO | WO 98/55062 | 12/1998 |
| WO | WO 99/17926 | 4/1999 |
| WO | WO 99/24519 | 5/1999 |
| WO | WO 99/47590 | 9/1999 |
| WO | WO 99/60969 | 12/1999 |
| WO | WO 99/60970 | 12/1999 |
| WO | WO 99/60971 | 12/1999 |
| WO | WO 00/10500 | 3/2000 |
| WO | WO 00/29199 | 5/2000 |
| WO | WO 00/37003 | 6/2000 |
| WO | WO 00/37005 | 6/2000 |
| WO | WO 00/37009 | 6/2000 |
| WO | WO 00/37723 | 6/2000 |
| WO | WO 00/59429 | 10/2000 |
| WO | WO 01/00053 | 1/2001 |
| WO | WO 01/32116 | 5/2001 |
| WO | WO 01/49907 | 7/2001 |
| WO | WO 01/87214 | 11/2001 |
| WO | WO 02/34184 | 5/2002 |
| WO | WO 02/053667 A2 | 7/2002 |
| WO | WO 02/053668 A2 | 7/2002 |
| WO | WO 02/060690 | 8/2002 |
| WO | WO 02/085624 A1 | 10/2002 |
| WO | WO 2004/039907 A1 | 5/2004 |

\* cited by examiner

STRAND-REINFORCED COMPOSITE MATERIAL

BACKGROUND OF THE INVENTION

This invention is directed to elastic composite materials including elastomeric adhesive film reinforced with elastic strands which significantly improves tension decay and adhesion properties of the material.

Personal care garments often include elasticized portions to create a gasket-like fit around certain openings, such as waist openings and leg openings. Laminates made from conventional elastic strands and elastic attachment adhesive are often used to create such elasticized portions. However, such laminates can be rough and uncomfortable. Furthermore, such laminates may cause red-marking on a wearer's skin if the fit is too tight and may result in leakage from the garment if the fit is too loose.

Multifunctional adhesive, such as elastic adhesives are currently recognized as suitable and desirable for use in the manufacture of personal care articles. More particularly, elastic adhesives can be used to bond facing materials, such as spunbond, to one another while simultaneously elasticizing the resulting laminate. The resulting laminate can be used to form an elastomeric portion of an absorbent article, such as a region surrounding a waist opening and/or a leg opening.

Current elastic adhesives, when used in combination with spunbond layers to form spunbond laminates, display noticeable tension decay and relatively poor adhesion properties.

There is a need or desire for an elastomeric laminate that can be used to create elasticized portions of a personal care garment, wherein the laminate does not display high tension decay or delamination. There is a further need or desire for an elastomeric laminate that possesses a soft feel and comfortable fit, while providing adjustable tension to minimize leakage.

SUMMARY OF THE INVENTION

In response to the discussed difficulties and problems encountered in the prior art, a new elastomeric composite has been discovered.

The present invention is directed to elastic composites, and laminates incorporating such elastic composites, having superior elastic and adhesion properties. These composites and laminates are particularly suitable for use in personal care product applications.

The elastic composites of the invention are made up of a combination of extruded reinforcing strands and elastomeric adhesive film. A layer of spunbond or other facing material can be laminated along both surfaces of the film to provide the elastic composite laminates of the invention. The combination of reinforcing strands and the elastomeric adhesive film significantly and advantageously reduces the rate and extent of tension decay, as well as improving adhesion properties of the spunbond laminates compared to spunbond laminates including elastomeric adhesive film without reinforcing strands. Furthermore, the reinforcing strands enable the composite tension to be tunable while preserving the soft feel and aesthetic properties of the laminate.

The invention also includes a method of making these elastic composites and elastic composite laminates. The method includes, optionally, the steps of tuning the tension in the composite by extruding some elastic strands at a greater tension than other elastic strands and incorporating the extruded elastic strands into an elastomeric adhesive film. The elastic strands can be extruded onto one chill roll while the elastomeric adhesive film is extruded onto another chill roll.

The tension in the elastic strands can be adjusted by the manner in which the strands are stretched. For example, to create greater tension, the strands can be stretched to a greater extent before incorporation with the elastomeric adhesive film. Another way to adjust tension is to adjust the add-on rate of the strands. Alternatively, or in addition to these methods of adjusting tension, the strands may vary in thickness and/or may vary in composition.

Once the elastic strands are adhered onto and partially embedded in the elastomeric adhesive film, a facing material such as a nonwoven web can be laminated to both surfaces of the elastomeric adhesive film.

With the foregoing in mind, it is a feature and advantage of the invention to provide elastic composites and elastic composite laminates having controlled tension. The invention also includes methods of making such elastic composites and elastic composite laminates.

DEFINITIONS

Figure 1:
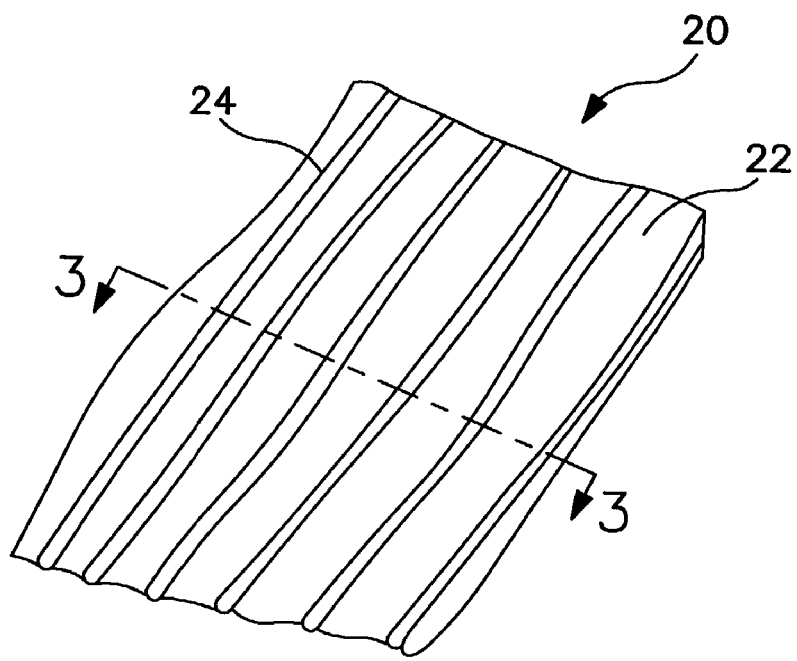
FIG. 1 is a plan view of an elastic composite of the invention.

Within the context of this specification, each term or phrase below will include the following meaning or meanings.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastic tension" refers to the amount of force per unit width required to stretch an elastic material (or a selected zone thereof) to a given percent elongation.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Elongation" refers to the capability of an elastic material to be stretched a certain distance, such that greater elongation refers to an elastic material capable of being stretched a greater distance than an elastic material having lower elongation.

"Extruded" refers to a material that is processed through an extrusion die or a slot coat die connected to an extruder or a melt tank.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Garment" includes personal care garments, medical garments, and the like. The term "disposable garment" includes garments which are typically disposed of after 1-5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"Layer" when used in the singular can have the dual meaning of a single element or a plurality of elements.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Strand" refers to an article of manufacture whose width is less than a film and is suitable for incorporating into a film, according to the present invention.

"Stretchable" means that a material can be stretched, without breaking, by at least 50% (to at least 150% of its initial (unstretched) length) in at least one direction, suitably by at least 100% (to at least 200% of its initial length), desirably by at least 150% (to at least 250% of its initial length). The term includes elastic materials as well as materials that stretch but do not significantly retract. The percentage stretch of strands and films is calculated by the percentage difference between a primary chill roll speed and a final nip roll speed. For example, in FIG. 6, if the first chill roller 42 is running at a speed of x and the nip rollers 58 and 60 are running at a speed of 6x, the strands and/or film being stretched between the first chill roller 42 and the nip rollers 58, 60 are being stretched 600%.

"Thermoplastic" describes a material that softens and flows when exposed to heat and which substantially returns to a nonsoftened condition when cooled to room temperature.

"Thermoset" describes a material that is capable of becoming permanently cross-linked, and the physical form of the material cannot be changed by heat without the breakdown of chemical bonds.

"Vertical filament stretch-bonded laminate" or "VF SBL" refers to a stretch-bonded laminate made using a continuous vertical filament process, as described herein.

These terms may be defined with additional language in the remaining portions of the specification.

DETAILED DESCRIPTION OF THE PRESENTLY PREFERRED EMBODIMENTS

The present invention is directed to elastic composites and elastic composite laminates having superior elastic and adhesion properties. The composites and laminates can be incorporated into any suitable article, such as personal care garments, medical garments, and industrial workwear garments. More particularly, the elastic composites and elastic composite laminates are suitable for use in diapers, training pants, swim wear, absorbent underpants, adult incontinence products, feminine hygiene products, protective medical gowns, surgical medical gowns, caps, gloves, drapes, face masks, laboratory coats, and coveralls.

A number of elastomeric components are known for use in the design and manufacture of such articles. For example, disposable absorbent articles are known to contain elasticized leg cuffs, elasticized waist portions, and elasticized fastening tabs. The elastic composites and laminates of this invention may be applied to any suitable article to form such elasticized areas.

As shown in FIG. 1, an elastomeric composite 20 of the invention includes an elastomeric adhesive film 22 with a number of elastic reinforcing strands 24 adhered to and partially embedded therein.

Tension within the elasomeric composite 20 may be controlled through percentage stretch of the strands 24 prior to adhesion to the elastomeric adhesive film 22, through percentage stretch of the film 22 prior to adhesion to the strands 24, and/or through the amount of strand add-on or thickness, with greater stretch and greater add-on or thickness each resulting in higher tension. Tension can also be controlled through selection of the film composition, selection of the strand composition, and/or by varying strand geometries and/or spacing between strands. It will be appreciated that the strands 24 may be laid out periodically, non-periodically, and in various spacings, groupings, and sizes, according to the effect desired from the composite 20 and the use to which it is put.

Figure 2:
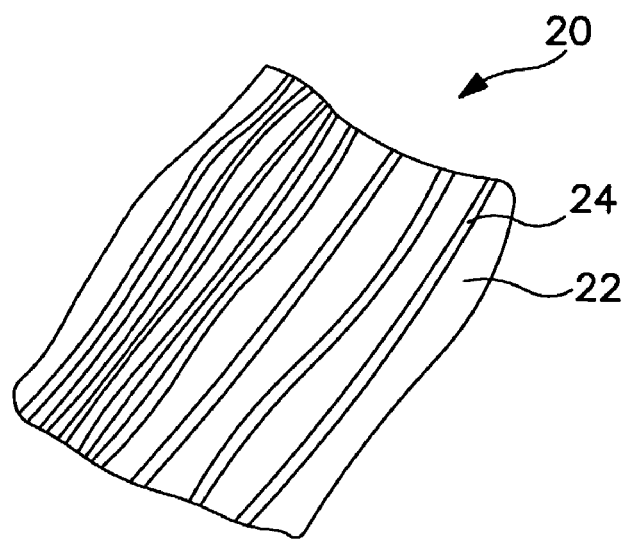
FIG. 2 is a plan view of another embodiment of an elastic composite of the invention.
Figure 3:
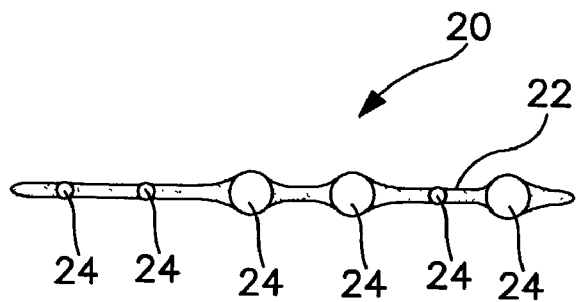
FIG. 3 is a cross-sectional view, taken along line 3-3 of FIG. 1, of another embodiment of an elastic composite of the invention.

As shown in FIG. 2, for example, a group of strands 24 in one region of the composite 20 can be spaced apart much more closely than another group of strands 24, resulting in greater tension in the region in which the strands 24 are more closely spaced. As another example, FIG. 3 illustrates a cross-sectional view of the composite 20 having unequally sized elastic strands 24 with some strands having a larger diameter, and thus higher tension, than others. While referred to as being of different diameter, it will be appreciated that the strands 24 need not be circular in cross-section within the context of this invention. Furthermore, the strands 24 of different size or composition may be intermingled within groupings in regular or irregular patterns.

The elastomeric adhesive film 22 is suitably made up of an elastomeric, hot melt, pressure-sensitive adhesive having an adhesive bond strength, as determined by the test method set forth below, of at least 50 grams force per inch (2.54 cm) width, suitably of at least 100 grams force per inch (2.54 cm) width, alternatively of at least 300 grams force per inch (2.54 cm) width, alternatively of at least from about 100 grams force per inch (2.54 cm) width to about 400 grams force per inch width. An example of a suitable elastomeric adhesive film 22 may be made up of 35 wt % PICOLYTE S115 and 65 wt % KRATON G2760. The elastomeric, hot melt, pressure-sensitive adhesive may be applied to a chill roll or similar device, in the form of a strand or ribbon. The strand or ribbon is then stretched and thinned to form the film 22. The film suitably has a thickness of about 0.001 inch (0.025 mm) to about 0.05 inch (1.27 mm), alternatively of from about 0.001 inch (0.025 mm) to about 0.01 inch (0.25 mm), and a width of from about 0.05 inch (1.27 mm) to about 3.0 inches (7.62 cm), alternatively of from about 0.5 inch (1.27 cm) to about 1.5 inches (3.81 cm). The elastomeric, adhesive film 22 may also be capable of imparting barrier properties in an application.

Suitable elastomeric, hot melt, pressure-sensitive adhesives from which the elastomeric adhesive film 22 may be made include elastomeric polymers, tackifying resins, plasticizers, oils and antioxidants.

One particular formulation of the elastomer adhesive film 22 includes a base polymer and a tackifier resin. The composition may also include additional additives. The choice of polymer and tackifier is important, as is the ratio of polymer or copolymers to tackifier. Another important consideration is the ratio of additives to tackifier.

The base polymer suitably has a styrene content of between about 15% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS), styrene-butadiene-styrene (SBS) block copolymer, as well as combinations of any of these. One example of a suitable SEPS copolymer is available from Kraton Polymers of Belpre, Ohio, under the trade designation KRATON® G 2760. One example of a suitable SIS copolymer is available from Dexco, a division of Exxon-Mobil, under the trade designation VECTOR™. Suitably, the film composition includes the base polymer in an amount between about 30% and about 65% by weight of the composition.

The tackifier may include hydrocarbons from petroleum distillates, rosin, rosin esters, polyterpenes derived from wood, polyterpenes derived from synthetic chemicals, as well as combinations of any of these. A key element of the film composition is a tackifier. An example of a suitable tackifier is available from Hercules Inc. of Wilmington, Del., under the trade designation PICOLYTE™ S115. Suitably, the composition includes the tackifier in an amount between about 30% and about 70% by weight of the composition.

Other additives may be included in the film composition as well. In addition to the adhesion provided by the tackifier, various additives may provide instantaneous surface tackiness and pressure sensitive characteristics as well as reduced melt viscosity. One example of a particularly suitable additive is paraffin wax, having a melting point of about 50 degrees Celsius.

Additionally, an antioxidant may be included in the film composition, suitably in an amount between about 0.1% and about 1.0% by weight of the composition. One example of a suitable antioxidant is available from Ciba Specialty Chemicals under the trade designation IRGANOX™ 1010.

The elastomeric adhesive film 22 suitably has an elongation of at least 50 percent, alternatively of at least 150 percent, alternatively of from about 50 percent to about 200 percent, and a tension force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width. Tension force, as used herein, is determined one minute after stretching the film to 100% elongation.

The elastomeric adhesive film 22 is capable not only of introducing a degree of elasticity to facing materials but is also capable of providing a construction adhesive function. That is, the film 22 adheres together the facing materials or other components with which it is in contact. It is also possible that the film does not constrict upon cooling but, instead, tends to retract to approximately its original dimension after being elongated during use in a product.

Materials suitable for use in preparing the elastic reinforcing strands 24 include raw polymers, a mixture of polymers, as well as tackified polymers. More specifically, the elastic reinforcing strands 24 may include diblock, triblock, tetrablock, or other multi-block elastomeric copolymers such as olefinic copolymers, including ethylene-propylene-diene monomer (EPDM), styrene-isoprene-styrene (SIS), styrene-butadiene-styrene (SBS), styrene-ethylene/butylene-styrene (SEBS), or styrene-ethylene/propylene-styrene (SEPS), which may be obtained from the Kraton Polymers of Belpre, Ohio, under the trade designation KRATON® elastomeric resin or from Dexco, a division of Exxon-Mobil, under the trade designation VECTOR® (SIS polymers); polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; polyisoprene; cross-linked polybutadiene; and single-site or metallocene-catalyzed polyolefins having density less than about 0.89 grams/cubic centimeter, available from Dow Chemical Co. under the trade name AFFINITY®. The elastic reinforcing strands 24 may also include a tackifier. The tackifier may include hydrocarbons from petroleum distillates, rosin, rosin esters, polyterpenes derived from wood, polyterpenes derived from synthetic chemicals, as well as combinations of any of these.

A number of block copolymers can also be used to prepare the elastic reinforcing strands 24 used in this invention. Such block copolymers generally include an elastomeric mid-block portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic strands 24 can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied to the strands in the same manner as thermoplastic polymers. As another alternative, the elastic strands 24 can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers useful in this invention include at least two substantially polystyrene endblock portions and at least one substantially ethylene/butylenes mid-block portion. A commercially available example of such a linear block copolymer is available from Kraton Polymers under the trade designation KRATON® G1657 elastomeric resin. Another suitable elastomer is KRATON® G2760. Yet another suitable elastomer is an SIS triblock copolymer available from Dexco, a division of Exxon-Mobil, under the trade designation VECTOR®.

The elastic reinforcing strands 24 may also contain blends of elastic and inelastic polymers, or of two or more elastic polymers, provided that the blend exhibits elastic properties. The strands 24 are substantially continuous in length. The strands 24 may have a circular cross-section but, as previously mentioned, may alternatively have other cross-sectional geometries such as elliptical, rectangular, triangular or multi-lobal. In one embodiment, one or more of the elastic reinforcing strands 24 may be in the form of elongated, rectangular strips produced from a film extrusion die having a plurality of slotted openings.

Figure 4:
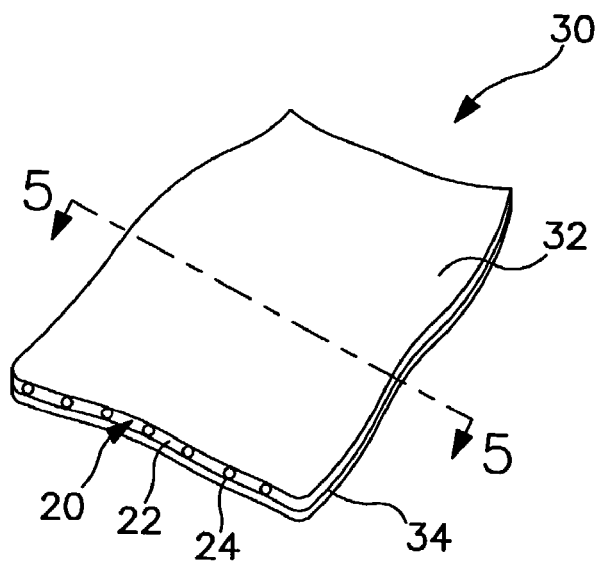
FIG. 4 is a plan view of an elastic composite laminate of the invention.
Figure 5:
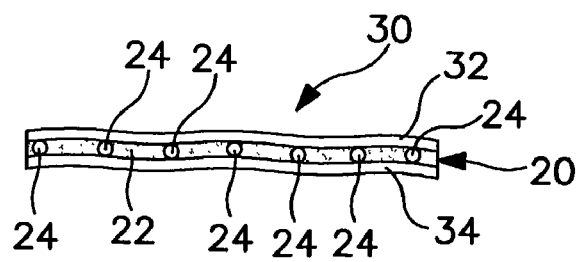
FIG. 5 is a cross-sectional view, taken along line 5-5 of FIG. 4, of another embodiment of an elastic composite laminate of the invention.

The elastic composite laminates 30 of the invention include the above-described elastic composites 20 sandwiched between a first facing sheet 32 and a second facing sheet 34, as shown in FIGS. 4 and 5. Facing materials may be formed using conventional processes, including the spunbond and meltblowing processes described in the DEFINITIONS. For example, the facing sheets 32, 34 may each include a spunbonded web having a basis weight of about 0.1-4.0 ounces per square yard (osy), suitably 0.2-2.0 osy, or about 0.4-0.6 osy. As another example, the facing sheets 32, 34 may each include a non-porous polyolefin film, such as outer cover material, or a combination of film and spunbond material. Two or more facing sheets 32, 34 may be present in the composite 20. The facing sheets 32, 34 may include the same or similar materials or different materials. Examples of suitable types of facing sheet 32, 34 combinations include at least one sheet of spunbond and at least one sheet of film, or two sheets of film, or two sheets of spunbond.

If the facing sheets 32, 34 are to be applied to the composite 20 without first being stretched, the facing sheets may or may not be capable of being stretched in at least one direction in order to produce an elasticized area. For example, the facing sheets could be necked, or gathered, in order to allow them to be stretched after application of the elastic composite. Various post treatments, such as treatment with grooved rolls, which alter the mechanical properties of the material, are also suitable for use.

Figure 6:
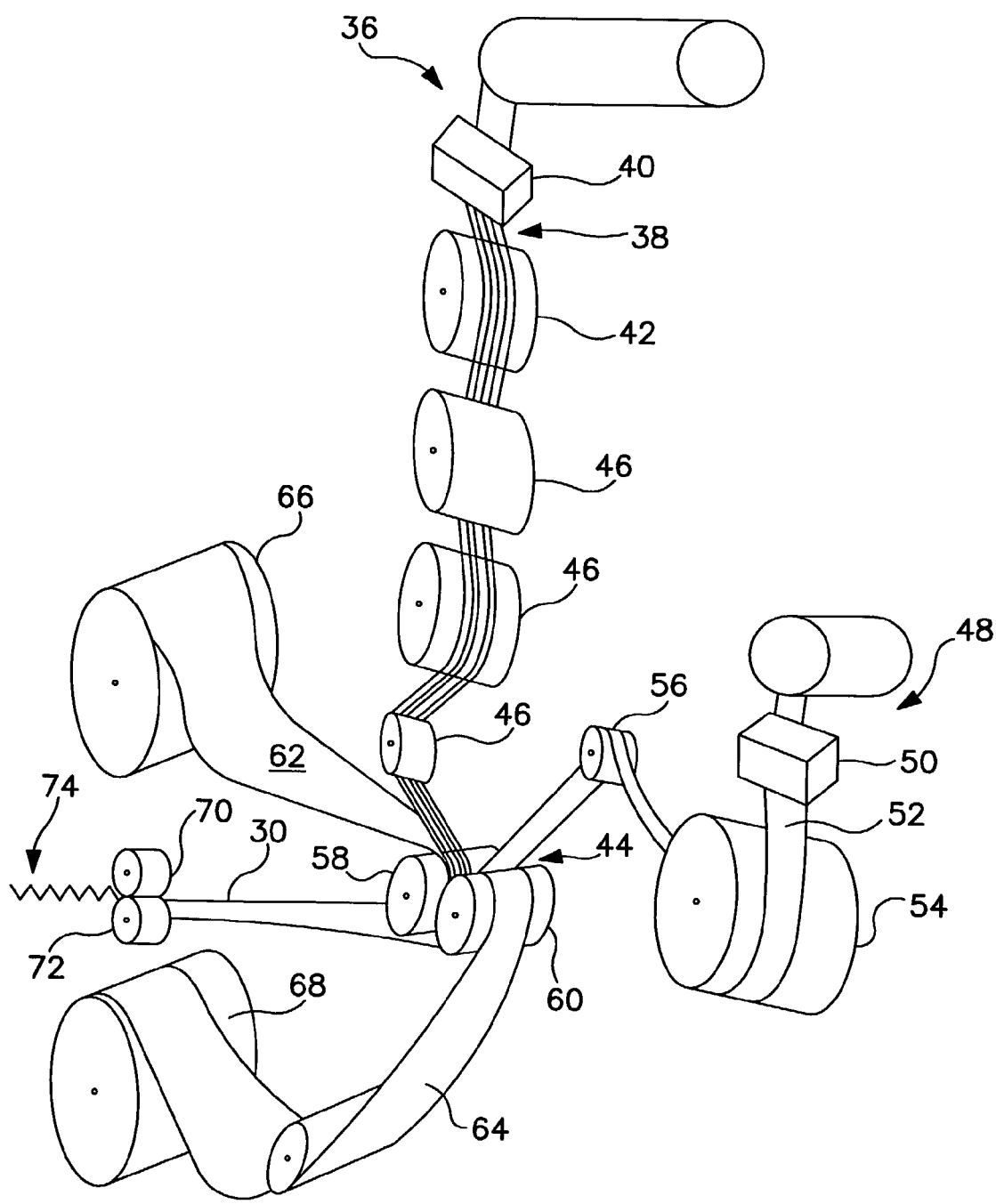
FIG. 6 illustrates a representative process for making the elastic composites and elastic composite laminates of the invention.

FIG. 6 illustrates a method and apparatus for making an elastic composite laminate 30 of the invention. While FIG. 6 illustrates a composite VF SBL process it will be appreciated that other processes consistent with the present invention may be used. A first extruder 36 produces reinforcing strands of elastic material 38 through a filament die 40. The strands 38 are fed to a first chill roller 42 and stretched while conveyed vertically towards a nip 44 by one or more first fly rollers 46 in the strand-producing line. For example, the strands may be stretched between about 300% and about 1000%; alternatively, the strands may be stretched between about 500% and about 800%. Another process parameter is the add-on rate. More specifically, the elastic strands may be adhered to, and partially embedded in, the elastomeric adhesive film at an add-on rate of between about 5 and about 50 grams per minute before stretching.

A second extruder 48 using a slotted film die 50 produces the elastomeric adhesive film 52, which is fed onto a second chill roller 54 and conveyed to one or more second fly rollers 56 towards the nip 44. The film 52 may be stretched down to a narrower width and thinned by the second fly rollers 56 during its passage to the nip 44. The nip 44 is formed by opposing first and second nip rollers 58, 60. The elastic composite 20 is formed by adhering the strands 38 to the elastomeric adhesive film 52 in the nip 44.

Figure 7:
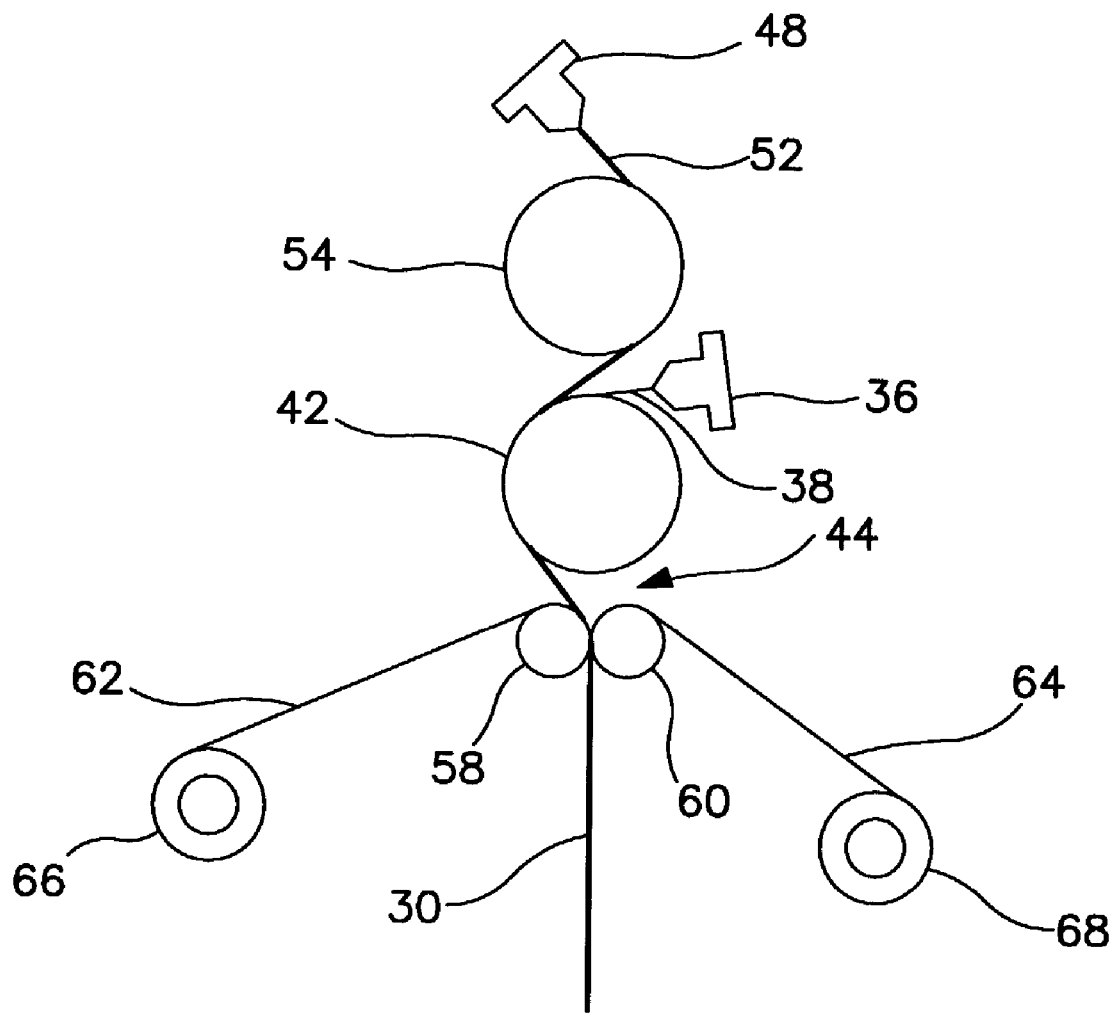
FIG. 7 is a schematic view of another process for making the elastic composites and elastic composite laminates of the invention.

FIG. 7 illustrates a VF SBL process in which no fly rollers 46, 56 are used. Instead, the elastomeric adhesive film 52 is extruded onto chill roller 54. The strands 38 are extruded onto chill roller 42 where the strands 38 and the elastomeric adhesive film 52 converge. The strands 38 and the elastomeric adhesive film 52 are stretched between the chill rollers 42, 54 and the nip 44. Except for the lack of fly rollers, the processes of FIGS. 6 and 7 are similar. In either case, the strands 38 and the elastomeric adhesive film 52 together are laminated between a first facing layer 62 and a second facing layer 64 at the nip 44.

In order to form the elastic composite laminate 30, first and second rolls 66 and 68, respectively, of spunbond facing material or other suitable facing material are fed into the nip 44 on either side of the elastic composite and are bonded by the adhesive present in the elastic composite. The facing material might also be made in situ rather than unrolled from previously-made rolls of material. While illustrated as having two lightweight gatherable spunbond facings, it will be appreciated that only one facing material, or various types of facing materials, may be used. The elastic composite laminate 30 can be maintained in a stretched condition by a pair of tensioning rollers 70, 72 downstream of the nip 44 and then relaxed as at Ref. No. 74 (FIG. 6).

Figure 8:
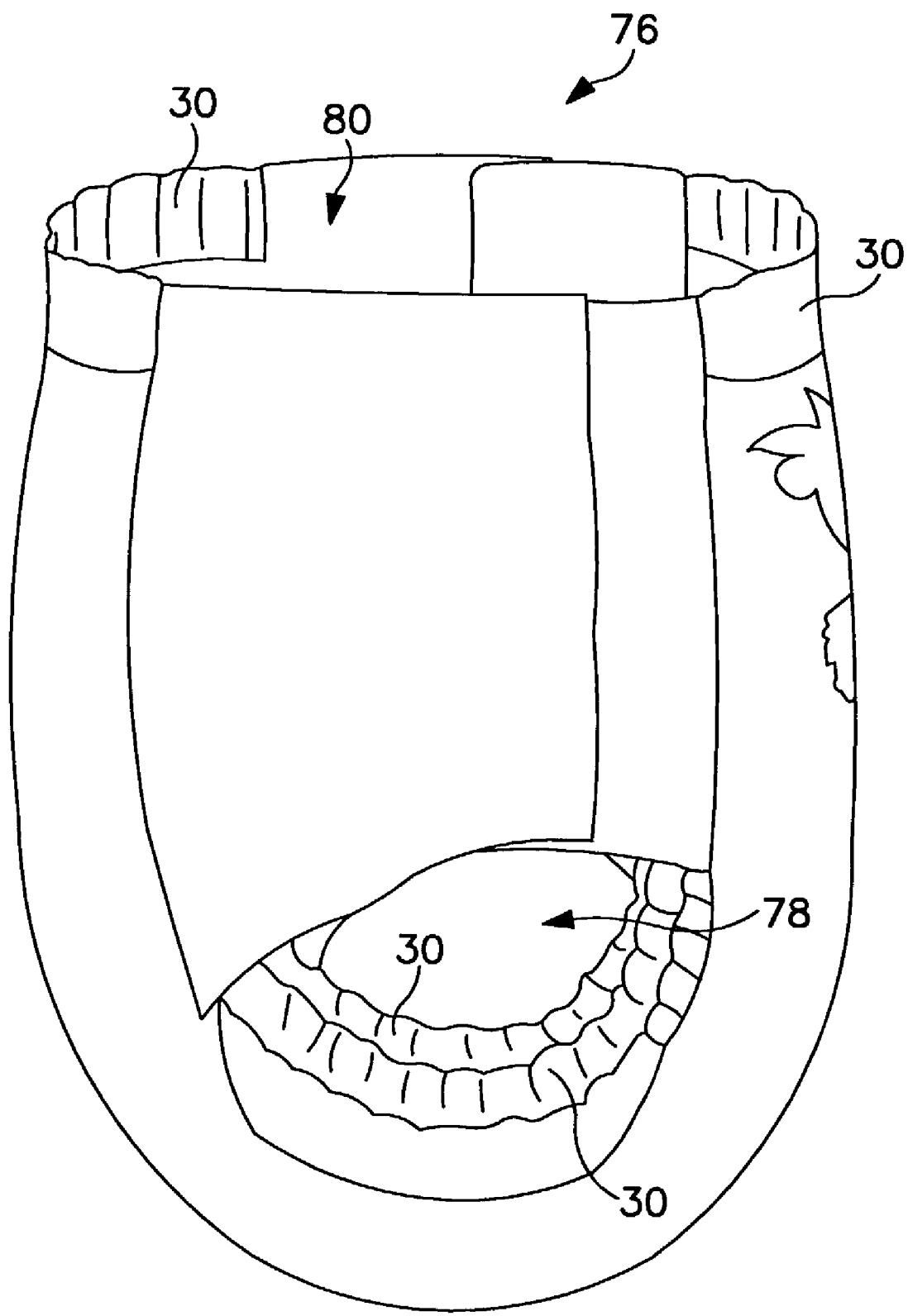
FIG. 8 is a perspective view of a garment having an elastic composite laminate around the leg openings and waist opening.

The resulting elastic composites and elastic composite laminates are particularly useful in providing elasticity in personal care absorbent garments 76, as shown in FIG. 8. More specifically, as shown in FIG. 8, the elastic composite laminates 30 are particularly suitable for use in providing a gasket-like fit around leg openings 78 and waist openings 80. The laminates of this invention are less likely to undergo tension decay or delamination compared to similar laminates lacking the reinforcing strands, as demonstrated in the example below. Furthermore, the reinforcing strands enable the composite tension to be tunable while preserving the soft feel and aesthetic properties of the laminate. Thus, elastic composite laminates can be produced with a desired fit or gasket-like quality without causing red marks on a wearer's skin due to excessive tension, while preserving the soft and gentle feel and improved adhesion of the laminate.

Test Methods

Adhesive Bond Strength

The adhesive bond strength of the elastomeric adhesive film of the present invention is determined as follows. A test sample of the elastic composite laminate having dimensions of about 2.0 inches (5.08 cm) wide by about 4.0 inches (10.16 cm) long, or as large as possible up to this size, is used for testing. The adhesive bond strength is determined through the use of a tensile tester, such as a SINTECH tensile tester commercially available from the Sintech Co., Carry, N.C., Model No. II. A 90 degree peel adhesion test is run in order to determine the grams of force needed to pull apart the first and second layers of facing sheet of the laminate. Specifically, 1.25 inches (3.175 cm) or more of the 4-inch length of the test sample has the first and second layers of facing sheet peeled apart. The first facing sheet is then clamped in the upper jaw of the tensile tester, and the second facing sheet is clamped in the lower jaw of the tensile tester. The tensile tester is set to the following conditions:

Crosshead speed: 300 millimeters per minute

Full-scale load: 5,000 grams

Start measurements: 10 millimeters

Gauge length (jaw spacings): 1.0 inch (2.54 cm)

The Instron tensile tester is then engaged. The test is terminated after approximately 100 millimeters on a 2-inch by 2-inch sample. Twenty data points per second are collected for a total of about 400 data points. The average of these data points is reported as the adhesive bond strength. The results from the tensile tester are normalized to a sample having a width of 1 inch. At least three test samples are subjected to the above testing with the results being averaged and normalized to produce the reported adhesive bond strength.

Elongation

The elongation of an elastic composite laminate according to the present invention is suitably determined as follows. A 1-inch wide by 4-inch long sample of the laminate is provided. The central 3-inch (7.62 cm) area of the sample is marked. The test sample is then stretched to its maximum length, and the distance between the marks is measured and recorded as the "stretched to stop length." The percent elongation is determined according to the following formula:

$$\{(\text{stretched to stop length (in inches)})-3\}/3\times 100$$

If a 1-inch by 4-inch area is not available, the largest sample possible (but less than 1-inch by 4-inches) is used for testing with the method being adjusted accordingly.

Tension Force

The tension force of an elastic composite laminate according to the present invention is determined on a test sample of the laminate having a width of 1 inch (2.54 cm) and a length of 3 inches (7.62 cm). A test apparatus having a fixed clamp and an adjustable clamp is provided. The adjustable clamp is equipped with a strain gauge commercially available from S. A. Mieier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 90 percent of its elongation (as determined by the test method set forth above). The tension force is read from the digital force gauge after 1 minute. At least three samples of the elasticized area are tested in this manner with the results being averaged and reported as grams force per inch width.

EXAMPLE 1

In this example, a strand-reinforced laminate material (sample B) was made in accordance with the invention and the tension decay properties were compared to a control (sample A) having the same elastomeric adhesive film composition without the elastic strands. In each case, the film add-on before stretching to 800% was 80 gsm and the elastomeric adhesive film composition was a mixture of 35 wt % PICOLYTE S115 and 65% KRATON G2760, to which 10% Hercules PICOLYTE S25 was added. More particularly, the elastic adhesive film underwent process elongation of between 500% and 800%, resulting in an output basis weight of between 70 and 120 grams per square meter (gsm) before stretching onto a chill roll having a temperature of 10 to 15 degrees Celsius, from a melt tank having a temperature of up to 400 degrees Fahrenheit.

The control spunbond/film/spunbond laminate sample (sample A) was made without any reinforcing strands. The test sample (sample B) was reinforced with VFL extruded strands of tackified SBL styrenic block copolymer available under the trade designation KRATON® G 2760 from Kraton Polymers, adhered to the elastic adhesive film. The test sample was prepared by extruding the strands and the elastomeric adhesive film on separate chill rolls. The die configuration through which the strands were extruded had 12 holes per inch with a 0.030 inch diameter opening. The output of the strands in terms of grams per minute (gpm) was 29.5 gpm for 120 strands per 10-inch die width, extruded on a chill roll at a speed of 6-8 feet per minute. Following the chill rolls, the strands and film were independently stretched to 700%. Thereafter, the film and strands were combined with spunbond webs on each side and laminated continuously to produce a material with tunable elastic properties.

Key process conditions versus physical properties (tension decay and adhesion) are summarized in Table 1. The tension decay was measured by first measuring the "green" tension at 100% elongation of a 2-inch wide, 5-inch long sample containing 24 strands (no strands in the case of the control sample). The tension reading was recorded from an electronic gauge one minute after clamping. After aging the samples at 130 degrees Fahrenheit for 1 day, the "aged" tension was then measured in the same manner as the green tension and the resulting aged tension was compared to the green tension to determine whether, or to what extent, tension decay occurred. The tension decay value is calculated by the percent difference between green and aged tension readings. A lower value of tension decay is indicative of improved elastic material performance. The tension decay of the strand-reinforced composite is much lower (12.8%) than in the case of no strands (62%). In either case the formulation has excellent adhesion properties with no indications of delamination after continued aging at 130 degrees Fahrenheit for 2 weeks. By exhibiting no delamination, it is meant that the laminates cannot be peeled apart without facing material failure. In this Example, delamination was visually determined as opposed to carrying out a peel test. Visual observations focused on the presence of any air pockets detected between layers of the laminate.

Tension of the elastic composite is tunable by varying the strand add-on and stretch percentage, with greater add-on and greater stretch both resulting in greater tension. Sample observations further reveal that soft feel and aesthetic properties of the laminates are preserved with the addition of the strands.

TABLE 1

Comparison of Tension Decay and Adhesion Properties of Novel Elastic Composite Laminates

| Sample | Output of extruded strands (gpm) | Strand process stretch (%) | Green tension (grams), 2-inch wide sample | Aged tension (grams), 1 day at 130° F. | Tension decay (%) | Aged sample observations |
|---|---|---|---|---|---|---|
| A (control) | None | — | 340 | 130 | 62.0 | No delamination |
| B (stranded composite) | 29.5 | 700 | 350 | 305 | 12.8 | No delamination |

EXAMPLE 2

In this example, the strand-reinforced laminate material (sample B) of Example 1 was incorporated into the leg cuff portion of a personal care garment, as indicated by the reference number 30 in FIG. 8. The "in-product" tension properties were evaluated and compared to conventional spunbonded laminates (SBL) and Lycra laminates (including Lycra strands adhered with elastic attachment adhesive). The "in-product" tension values of the elasticized laminate composite portion of the personal care garment are shown in Table 2 and were measured as follows.

The garment was extended flat on a lightbox and clamped at one end while a 1000 gram weight in the form of a bar was attached at the other end, resulting in stretching of the material in the machine direction. Two marks corresponding to a discrete gauge length value in the range of 4-7 inches were placed on the stretched elastic portion. The weight was removed and the retracted elastic laminate composite was cut out from the product, normally as a 1-inch wide strip. The cut elastic strip was mounted in a Chantillon tension gauge and stretched to 90% of gauge length. The tension in grams was recorded after a one-minute waiting period. The elasticized strips were evaluated for tension before and after the product was worn at body temperature in order to evaluate the degree of tension decay as a result of wearing the article. A lower degree of tension decay (as measured by the percentage difference between post-wear and pre-wear) is indicative of a better performing elastic material. Tension measurements before and after wear show a significant drop for conventional SBL laminate control (−22%). The tension drop for the other control of conventional Lycra laminate was significant as well (−10%). However, the laminate made from the strand-reinforced elastomeric adhesive film of the invention had no tension loss and actually gained some tension as a result of wearing at body temperature. The elastic adhesive laminate of the invention with no tension loss provides superior gasketing performance compared to conventional materials.

TABLE 2

Comparative Tension of Laminates

| Material | Tension (grams), before wear | Tension (grams), after wear | % difference |
|---|---|---|---|
| SBL laminate | 127.5 | 104.5 | −22.0 |
| Lycra laminate | 120.8 | 109.4 | −10.0 |
| Strand-reinforced laminate | 141.5 | 144.6 | +2.1 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An elastomeric composite laminate, comprising:
   a plurality of extruded elastic strands adhered to an elastomeric adhesive film; and
   a first facing sheet bonded to a first surface of the elastomeric adhesive film and a second facing sheet bonded to a second surface of the elastomeric adhesive film.

2. The elastomeric composite laminate of claim 1, wherein the plurality of elastic strands comprises at least one of a group consisting of raw polymers, a mixture of polymers, and tackified polymers.

3. The elastomeric composite laminate of claim 1, wherein the plurality of elastic strands comprises at least one of a group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof.

4. The elastomeric composite laminate of claim 1, wherein the plurality of elastic strands comprises a tackifier including at least one type of hydrocarbon selected from a group consisting of petroleum distillates, rosin, rosin esters, polyterpenes derived from wood, polyterpenes derived from synthetic chemicals, and combinations thereof.

5. The elastomeric composite laminate of claim 1, wherein the elastomeric adhesive film comprises an elastomeric, hot melt, pressure-sensitive adhesive.

6. The elastomeric composite laminate of claim 1, wherein the plurality of elastic strands comprises between about 5% and about 50% by weight of the film and the elastic strands combined.

7. The elastomeric composite laminate of claim 1, wherein the plurality of elastic strands comprises between about 10% and about 35% by weight of the film and the elastic strands combined.

8. The elastomeric composite laminate of claim 1, wherein the plurality of elastic strands comprises between about 15% and about 25% by weight of the film and the elastic strands combined.

9. The elastomeric composite laminate of claim 1, wherein at least one of the first and second facing sheets comprises a spunbond web.

10. The elastomeric composite laminate of claim 1, wherein at least one of the first and second facing sheets comprises a film.

11. The elastomeric composite laminate of claim 1, further comprising:
a garment incorporating the elastomeric laminate into a structure of the garment.

12. The elastomeric composite laminate of claim 11, wherein the garment is one selected from a group consisting of personal care garments, medical garments, and industrial workwear garments.

13. The elastomeric composite laminate of claim 12, wherein the garment is one selected from a group consisting of diapers, training pants, swim wear, absorbent underpants, adult incontinence products, feminine hygiene products, protective medical gowns, surgical medical gowns, caps, gloves, drapes, face masks, laboratory coats, and coveralls.

14. An elastomeric composite laminate, comprising:
a plurality of extruded elastic strands at least partially embedded in an elastomeric adhesive film;
a first layer bonded to a first surface of the elastomeric adhesive film, the first layer comprising at least one of a nonwoven web and a film; and
a second layer bonded to a second surface of the elastomeric adhesive film, the second layer comprising at least one of a nonwoven web and a film.

15. The elastomeric composite laminate of claim 14, wherein the plurality of elastic strands comprises at least one of a group consisting of raw polymers, a mixture of polymers, and tackified polymers.

16. The elastomeric composite laminate of claim 14, wherein the plurality of elastic strands comprises at least one of a group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof.

17. The elastomeric composite laminate of claim 14, wherein the plurality of elastic strands comprises a tackifier including at least one type of hydrocarbon selected from a group consisting of petroleum distillates, rosin, rosin esters, polyterpenes derived from wood, polyterpenes derived from synthetic chemicals, and combinations thereof.

18. The elastomeric composite laminate of claim 14, wherein the elastomeric adhesive film comprises an elastomeric, hot melt, pressure-sensitive adhesive.

19. A garment having an elastomeric film composite therein which is made by a process comprising:
adhering a plurality of elastic strands to an elastomeric adhesive film such that the plurality of elastic strands is at least partially embedded in the elastomeric adhesive film.

20. The elastomeric composite laminate of claim 1, wherein the plurality of extruded elastic strands is at least partially embedded in the elastomeric adhesive film.

21. The elastomeric composite laminate of claim 14, wherein the plurality of elastic strands comprises between about 5% and about 50% by weight of the film and the elastic strands combined.

22. The elastomeric composite laminate of claim 14, wherein the plurality of elastic strands comprises between about 10% and about 35% by weight of the film and the elastic strands combined.

23. The elastomeric composite laminate of claim 14, wherein the plurality of elastic strands comprises between about 15% and about 25% by weight of the film and the elastic strands combined.

24. The elastomeric composite laminate of claim 14, wherein at least one of the first and second facing sheets comprises a spunbond web.

25. The elastomeric composite laminate of claim 14, further comprising:
a garment incorporating the elastomeric laminate into a structure of the garment.

26. The elastomeric composite laminate of claim 25, wherein the garment is one selected from a group consisting of personal care garments, medical garments, and industrial workwear garments.

27. The elastomeric composite laminate of claim 26, wherein the garment is one selected from a group consisting of diapers, training pants, swim wear, absorbent underpants, adult incontinence products, feminine hygiene products, protective medical gowns, surgical medical gowns, caps, gloves, drapes, face masks, laboratory coats, and coveralls.

28. The garment of claim 19, wherein the plurality of elastic strands comprises at least one of a group consisting of raw polymers, a mixture of polymers, and tackified polymers.

29. The garment of claim 19, wherein the plurality of elastic strands comprises at least one of a group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof.

30. The garment of claim 19, wherein the plurality of elastic strands comprises a tackifier including at least one type of hydrocarbon selected from a group consisting of petroleum distillates, rosin, rosin esters, polyterpenes derived from wood, polyterpenes derived from synthetic chemicals, and combinations thereof.

31. The garment of claim 19, wherein the elastomeric adhesive film comprises an elastomeric, hot melt, pressure-sensitive adhesive.

32. The garment of claim 19, wherein the process further comprises laminating a first facing sheet onto a first surface of the elastomeric adhesive film and laminating a second facing sheet onto a second surface of the elastomeric adhesive film.

33. The garment of claim 19, wherein the garment is one selected from a group consisting of personal care garments, medical garments, and industrial workwear garments.

34. The garment of claim 33, wherein the garment is one selected from a group consisting of diapers, training pants, swim wear, absorbent underpants, adult incontinence products, feminine hygiene products, protective medical gowns, surgical medical gowns, caps, gloves, drapes, face masks, laboratory coats, and coveralls.

* * * * *